(12) United States Patent
Beasley et al.

(10) Patent No.: US 8,864,676 B2
(45) Date of Patent: Oct. 21, 2014

(54) IMPLANTABLE MEDICAL SENSOR AND FIXATION SYSTEM

(75) Inventors: Rudy Beasley, Rohnert Park, CA (US); Erik Griswold, Penngrove, CA (US); James Calvin Allan, Santa Rosa, CA (US); George Patras, Greenfield, MN (US); Kamal Deep Mothilal, Minneapolis, MN (US); Albert Dunfee, Byfield, MA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 550 days.

(21) Appl. No.: 13/090,869

(22) Filed: Apr. 20, 2011

(65) Prior Publication Data
US 2012/0108986 A1 May 3, 2012

Related U.S. Application Data

(60) Provisional application No. 61/408,073, filed on Oct. 29, 2010, provisional application No. 61/437,198, filed on Jan. 28, 2011.

(51) Int. Cl.
| | | |
|---|---|---|
| *A61B 5/02* | (2006.01) | |
| *A61B 5/0215* | (2006.01) | |
| *A61N 1/372* | (2006.01) | |
| *A61B 5/00* | (2006.01) | |
| *A61B 5/0205* | (2006.01) | |
| *A61B 5/01* | (2006.01) | |
| *A61B 5/029* | (2006.01) | |

(52) U.S. Cl.
CPC ........... *A61B 5/6884* (2013.01); *A61N 1/37205* (2013.01); *A61B 5/0031* (2013.01); *A61B 5/0215* (2013.01); *A61B 5/6876* (2013.01); *A61B 5/02055* (2013.01); *A61B 2560/066* (2013.01); *A61B 5/01* (2013.01); *A61B 5/6879* (2013.01); *A61B 5/029* (2013.01)
USPC .......................................... 600/481; 600/486

(58) Field of Classification Search
CPC ... A61B 5/021; A61B 5/02141; A61B 5/0215
USPC .................................................. 600/485–499
See application file for complete search history.

(56) References Cited

U.S. PATENT DOCUMENTS

| 2,523,785 A | 9/1950 | Sereno |
| 3,905,070 A | 9/1975 | Macrae |

(Continued)

FOREIGN PATENT DOCUMENTS

| DE | 20 2005 001416 U1 | 3/2005 |
| EP | 0897690 | 2/1999 |

(Continued)

OTHER PUBLICATIONS

EPO, Int'l. Search Report & Written Opinion of the ISA for Appln. No. PCT/US2012/032770, Mar. 6, 2013.

*Primary Examiner* — Navin Natnithithadha
*Assistant Examiner* — Eric Messersmith

(57) ABSTRACT

An implantable medical device, such as a sensor for monitoring a selected internally detectable physiological parameter of a patient, is attached to a fixation member that is deployable within the patient to position and orient the sensor to enable it to perform its function. The fixation member may be configured to lie in a single plane when deployed or may be tubular in shape. The attachment of the housing and fixation member includes providing the fixation member with a linear attachment strut that is non-circular in cross section and providing the housing with external members that define an elongate channel, non-circular in cross section and receptive to the attachment strut. The attachment strut can be inserted transversely into the channel and the external member can be crimped over the strut to secure the housing and fixation member together.

13 Claims, 16 Drawing Sheets

(56) References Cited

U.S. PATENT DOCUMENTS

| | | |
|---|---|---|
| 4,760,849 A | 8/1988 | Kropf |
| 4,913,147 A | 4/1990 | Fahlstrom et al. |
| 5,147,330 A | 9/1992 | Kogel |
| 5,218,965 A | 6/1993 | Ring |
| 5,284,138 A | 2/1994 | Kujawski |
| 5,411,546 A | 5/1995 | Bowald et al. |
| 5,411,551 A | 5/1995 | Winston et al. |
| 5,415,630 A | 5/1995 | Gory et al. |
| 5,772,668 A | 6/1998 | Summers et al. |
| 5,800,520 A | 9/1998 | Fogarty et al. |
| 5,967,986 A | 10/1999 | Cimochowski et al. |
| 6,015,387 A | 1/2000 | Schwartz et al. |
| 6,024,764 A | 2/2000 | Schroeppel |
| 6,053,873 A | 4/2000 | Govari et al. |
| 6,159,156 A | 12/2000 | Van Bockel |
| 6,214,036 B1 | 4/2001 | Letendre et al. |
| 6,277,078 B1 | 8/2001 | Porat et al. |
| 6,309,350 B1 | 10/2001 | Van Tassel et al. |
| 6,331,163 B1 | 12/2001 | Kaplan |
| 6,371,928 B1 | 4/2002 | Mcfann et al. |
| 6,416,474 B1 | 7/2002 | Penner et al. |
| 6,442,413 B1 | 8/2002 | Silver |
| 6,468,301 B1 | 10/2002 | Amplatz et al. |
| 6,783,499 B2 | 8/2004 | Schwartz |
| 6,821,291 B2 | 11/2004 | Bolea et al. |
| 6,855,115 B2 | 2/2005 | Fonseca et al. |
| 6,908,464 B2 | 6/2005 | Jenkins et al. |
| 6,909,920 B2 | 6/2005 | Lokhoff et al. |
| 6,926,670 B2 | 8/2005 | Rich et al. |
| 6,932,837 B2 | 8/2005 | Amplatz et al. |
| 7,011,671 B2 | 3/2006 | Welch |
| 7,018,401 B1 | 3/2006 | Hyodah et al. |
| 7,181,261 B2 | 2/2007 | Silver et al. |
| 7,182,725 B2 | 2/2007 | Bonan et al. |
| 7,211,107 B2 | 5/2007 | Bruckheimer et al. |
| 7,240,516 B2 | 7/2007 | Pryor |
| 7,309,354 B2 | 12/2007 | Mathis et al. |
| 7,473,272 B2 | 1/2009 | Pryor |
| 7,481,771 B2 | 1/2009 | Fonseca et al. |
| 7,572,228 B2 | 8/2009 | Wolinsky et al. |
| 7,655,039 B2 | 2/2010 | Leanna et al. |
| 7,682,313 B2 | 3/2010 | Bodecker et al. |
| 7,726,663 B2 | 6/2010 | Mack et al. |
| 7,727,270 B2 | 6/2010 | Rucker |
| 7,769,420 B2 | 8/2010 | Silver et al. |
| 7,771,463 B2 | 8/2010 | Ton et al. |
| 7,797,053 B2 | 9/2010 | Atkinson et al. |
| 7,799,067 B2 | 9/2010 | Pryor |
| 7,801,626 B2 | 9/2010 | Moser |
| 7,801,627 B2 | 9/2010 | Haldeman |
| 2002/0147487 A1 | 10/2002 | Sundquist et al. |
| 2002/0151816 A1* | 10/2002 | Rich et al. .................... 600/547 |
| 2002/0161423 A1 | 10/2002 | Lokhoff et al. |
| 2002/0188207 A1 | 12/2002 | Richter |
| 2003/0023295 A1 | 1/2003 | Osypka |
| 2003/0032936 A1 | 2/2003 | Lederman |
| 2003/0125790 A1 | 7/2003 | Fastovsky et al. |
| 2003/0153966 A1 | 8/2003 | Taubert et al. |
| 2004/0044393 A1 | 3/2004 | Yarden et al. |
| 2004/0116992 A1 | 6/2004 | Wardle et al. |
| 2005/0033394 A1 | 2/2005 | Seifert et al. |
| 2005/0154321 A1 | 7/2005 | Wolinsky et al. |
| 2005/0187482 A1 | 8/2005 | O'Brien et al. |
| 2006/0047205 A1 | 3/2006 | Ludomirsky et al. |
| 2006/0122522 A1 | 6/2006 | Chavan et al. |
| 2006/0200030 A1 | 9/2006 | White et al. |
| 2006/0200031 A1 | 9/2006 | White et al. |
| 2006/0271166 A1 | 11/2006 | Thill et al. |
| 2006/0287700 A1 | 12/2006 | White et al. |
| 2006/0293741 A1 | 12/2006 | Johnson et al. |
| 2007/0129637 A1 | 6/2007 | Wolinsky et al. |
| 2007/0179583 A1 | 8/2007 | Goetzinger et al. |
| 2008/0071178 A1* | 3/2008 | Greenland et al. ............ 600/486 |
| 2008/0071248 A1 | 3/2008 | Delgado et al. |
| 2008/0167702 A1 | 7/2008 | Ransbury et al. |
| 2008/0176271 A1* | 7/2008 | Silver et al. .................... 435/29 |
| 2009/0018644 A1 | 1/2009 | Weber et al. |
| 2009/0105557 A1 | 4/2009 | Najafi et al. |
| 2009/0264991 A1 | 10/2009 | Paul et al. |
| 2009/0295383 A1 | 12/2009 | Gianchandani et al. |
| 2009/0309273 A1 | 12/2009 | Parker |
| 2010/0030321 A1 | 2/2010 | Mach |
| 2010/0161027 A1 | 6/2010 | Orr |

FOREIGN PATENT DOCUMENTS

| | | |
|---|---|---|
| EP | 0928598 | 8/2000 |
| EP | 1068836 | 1/2002 |
| EP | 1488735 | 6/2007 |
| WO | WO8303348 | 10/1983 |
| WO | WO0016686 | 3/2000 |
| WO | WO0059376 | 10/2000 |
| WO | WO0187137 | 11/2001 |
| WO | WO02054980 | 7/2002 |
| WO | WO2005067817 | 7/2005 |
| WO | WO2006062725 | 6/2006 |
| WO | WO2007057739 | 5/2007 |
| WO | WO2007082115 | 7/2007 |
| WO | WO2008057720 | 5/2008 |
| WO | WO2008060197 | 5/2008 |
| WO | WO2008144191 | 11/2008 |

* cited by examiner

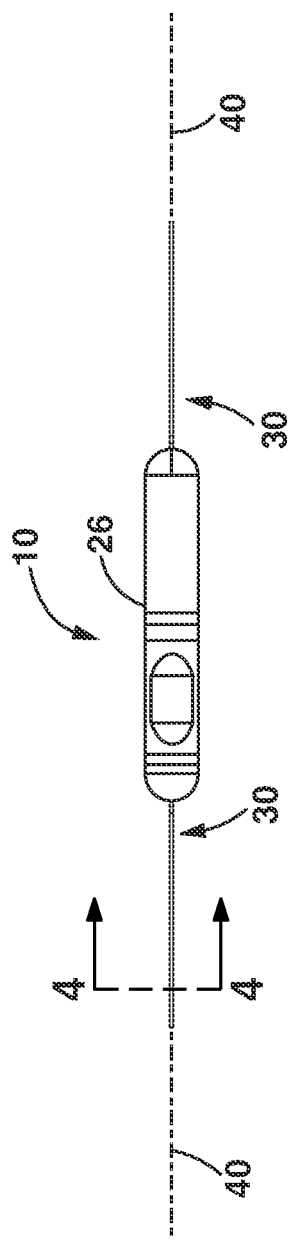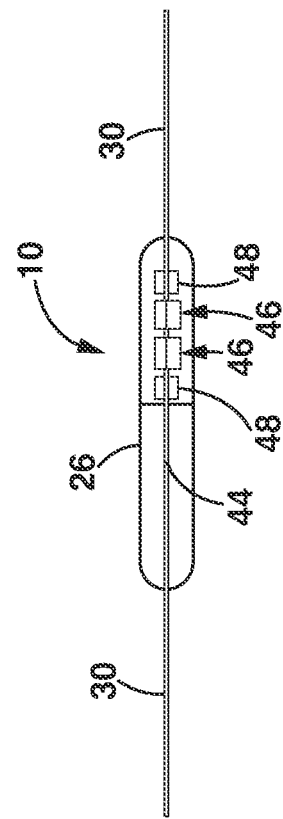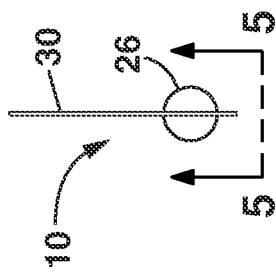

IMPLANTABLE MEDICAL SENSOR AND FIXATION SYSTEM

RELATED APPLICATIONS

This application claims priority to provisional U.S. Patent Application Ser. No. 61/408,073, filed Oct. 29, 2010, entitled Medical Device Fixation Attachment Mechanism and to provisional U.S. Patent Application Ser. No. 61/437,198, filed Jan. 28, 2011, entitled Communication Dipole for Implantable Medical Device.

FIELD OF THE INVENTION

The invention relates to implantable medical sensors and fixation of such sensors in body lumens.

BACKGROUND

Various implantable medical devices have been clinically implanted or proposed for therapeutically treating or monitoring one or more physiological conditions of a patient. Such devices may be adapted to monitor or treat conditions or functions relating to heart, muscle, nerve, brain, stomach, endocrine organs or other organs and their related functions. Advances in design and manufacture of miniaturized electronic and sensing devices have enabled development of implantable devices capable of therapeutic as well as diagnostic functions such as pacemakers, cardioverters, defibrillators, biochemical sensors, and pressure sensors, among others. Such devices may be associated with leads for electrical functions or may be wireless, with the ability to transmit data electronically either to another device implanted in the patient or to another device located externally of the patient, or both.

Although implantation of some devices requires a surgical procedure (e.g., pacemakers, defibrillators, etc.) other devices may be small enough to be delivered and placed at an intended deployment site in a relatively noninvasive manner, such as by a percutaneous delivery catheter. Depending on the nature, function and intended deployment site of the device, the manner in which the device is fixed in place and oriented in the body may affect the operation and accuracy of the device. Consequently, the means by which the device is fixed in place in the body can be a significant factor in its performance and utility.

By way of illustrative example, implantable miniature sensors have been proposed and used in blood vessels to measure directly the diastolic, systolic and mean blood pressures, as well as body temperature and cardiac output. Such direct in vivo measurement of hemodynamic parameters may provide significant information to clinicians to facilitate diagnostic and therapeutic decisions. If linked electronically to another implanted therapeutic device (e.g., a pacemaker), the data can be used to facilitate control of that device. Such sensors also, or alternatively, may be wirelessly linked to an external receiver. As one example, patients with chronic cardiovascular conditions, particularly patients suffering from chronic heart failure, may benefit from the use of implantable sensors adapted to monitor blood pressures. Promising indications have been reported for using such implantable sensors. Accurate knowledge of a patient's hemodynamic parameters can inform the decision whether to admit the patient to the hospital or whether the patient's condition can be managed with other therapies not requiring hospital admission. This is particularly so in connection with measurements of the blood pressure in the pulmonary artery that cannot be measured readily from an external location. Assessing a patient's pulmonary artery blood pressure is a critical factor in diagnosing the heart failure patient and determining how best to manage the patient. Typically, blood pressure in the pulmonary artery has been determined by using a balloon-tipped pulmonary artery catheter having a pressure measurement function and sold under the trademark SWAN-GANZ, which is inserted and navigated through the right side of the patient's heart and the pulmonary valve into the pulmonary artery, a procedure that requires hospitalization. It has been estimated that there are about five million patients in the United States who suffer from heart failure with approximately one million hospital admissions per year to assess and treat the condition. It would be desirable to provide a means by which such data could be obtained before admitting the patient to the hospital as the patient may experience an improved quality of life and it might avoid the necessity for and cost of hospitalization.

It is among the general objects of the invention to provide a minimally invasive, improved means for controllably placing and supporting an implantable sensor within a body lumen in a position, location and sensor element orientation that facilitates the operation of the device, in which the means includes a fixation member to which the sensor is mounted to achieve these objects.

SUMMARY OF THE INVENTION

In accordance with the invention, an implantable sensor is attached to a fixation member of wire-like construction that is expandable from a low profile configuration, in which a catheter can deliver it to the deployment site in the vessel, to an expanded configuration in which it is deployed in the vessel in engagement with the vessel wall. The fixation member may be formed from a highly resilient material, preferably one having superelastic properties and includes at least one linear attachment strut and at least one self-expandable portion. The sensor includes a housing with attachment elements adapted to receive the attachment strut in a manner that fixes the position of the sensor relative to the axis of the attachment strut and prevents the sensor housing from rotating about the strut. The housing of the sensor includes an elongate channel adapted to receive the attachment strut transversely. The channel may be defined in part by bendable tabs that are plastically deformed over the inserted attachment strut to secure the sensor housing and strut together. In another aspect of the invention the wire-like fixation member, including the expandable portion, is formed to lie in a single plane when expanded. The fixation member is dimensioned with respect to the intended deployment site so that when expanded it will engage the wall of the vessel at diametrically opposed locations in the vessel sufficiently to secure the fixation member and sensor housing to which it is attached, in place. In one embodiment of the invention the sensor housing may contain pressure sensing components including an externally exposed sensing element and is mounted to the fixation member such that, when the fixation member is deployed, the sensing element of the sensor will face along a direction generally perpendicular to the plane of the fixation member, to face inwardly toward the center of the vessel lumen and be exposed fully to the pressure within the vessel. In another embodiment the fixation member and sensor are arranged so that the sensing element faces generally parallel to the plane of the fixation member. The fixation member also may be configured to position the sensor housing and, particularly, the sensing element, away from the vessel wall to lessen the risk of turbulent flow through the vessel.

In a further aspect of the invention the fixation member includes at least one continuous loop integral with the attachment strut with the loop being non-circular, preferably somewhat teardrop-shaped, having narrow and broad ends. The narrow end is toward the middle of the fixation member with the broader portion located at the end of the fixation member where it can be engaged by a delivery device. The fixation member is formed from a superelastic material and the loop is compressible to a low delivery profile shape of a pair of approximately parallel wires. The narrow end of the teardrop loop is adapted to avoid excessive strain on that portion of the loop when the loop is compressed to its low profile, delivery shape.

In a further aspect of the invention a delivery device for the sensor assembly may include a catheter on which the sensor assembly is mounted in its low profile configuration. The assembly is retained on the catheter shaft by a pair of longitudinally spaced, helical retention elements, secured to a rotatable inner shaft contained in the catheter shaft. The sensor assembly is loaded so that each helical retention element has a free end that protrudes out of an exit aperture in the catheter shaft. The protruding end wraps about one of the compacted loops of the sensor assembly and reenters the shaft through a second aperture circumferentially spaced from the first. When the delivery device has been navigated to the intended deployment site the inner shaft is rotated in a direction to withdraw the free ends into the catheter shaft thus releasing the fixation member and enabling it to self-expand. The loops of the sensor assembly may be released simultaneously or may be released sequentially to enable the clinician to confirm proper placement of one of the loops before releasing the other. The arrangement enables the sensor assembly to be recaptured and repositioned should that be indicated.

In another aspect of the invention a sensor housing may be secured to fixation members that have a tubular shape by forming the fixation member to include at least one linear attachment strut that can be received transversely in the channel of the housing and by then mechanically securing the strut in the channel.

It should be understood that although the invention is described principally in the context of fixing a sensor in the pulmonary artery tree to measure blood pressure, the invention is not limited to use in that context. The principles of the invention may be used to make implantable sensors assemblies adapted to measure and monitor any of a variety of physiological parameters.

DESCRIPTION OF THE DRAWINGS

The advantages, features and objects of the invention will be appreciated more fully from the following description and accompanying drawings in which:

FIG. 3 is a plan view of the sensor assembly shown in FIG. 2;

FIG. 4 is an end view of the sensor assembly shown in FIG. 2 as seen along the line 4-4 of FIG. 3;

FIG. 5 is a bottom view of the sensor assembly shown in FIG. 2 as seen along the line 5-5 of FIG. 4;

DESCRIPTION OF THE ILLUSTRATIVE EMBODIMENTS

The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

Figure 1:
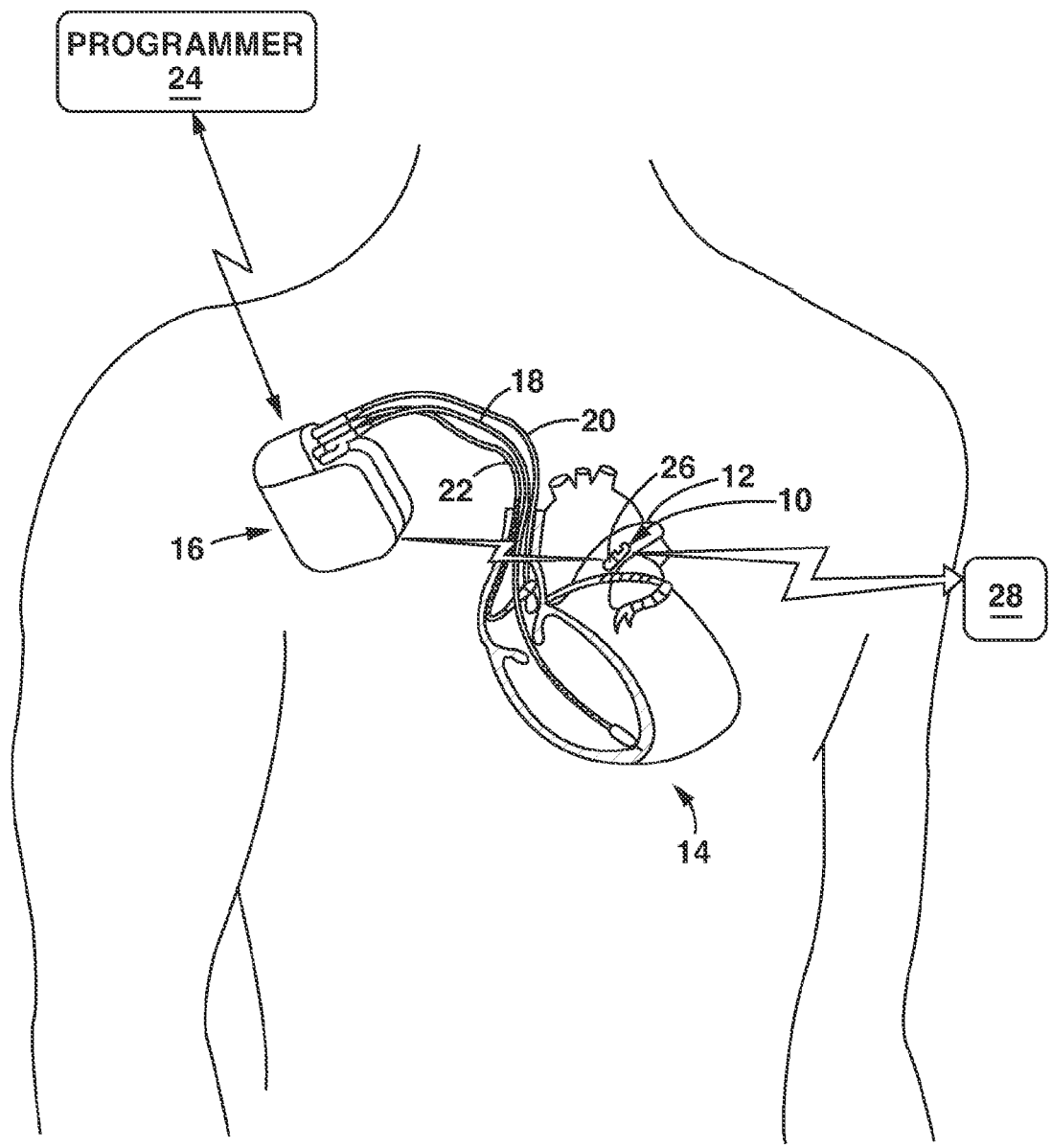
FIG. 1 is a diagrammatic illustration of a human patient depicting the locations of implantable medical devices including, for example, a pacemaker or defibrillator and a wireless sensor assembly placed in the pulmonary artery of the patient.

FIG. 1 illustrates, diagrammatically, a patient with implanted medical devices including a sensor assembly 10 implanted, for example, in the patient's pulmonary artery 12 through which blood flows from the heart 14 to the lungs, and another device, such as a pacemaker, defibrillator or the like, indicated generally at 16. For purposes of this description, knowledge of cardiovascular anatomy is presumed and details are omitted except to the extent necessary or desirable to explain the context of the invention. The device 16 may have a number of leads 18, 20, 22 that are placed in electrical contact with selected portions of the cardiac anatomy in order to perform the functions of the device 16 as is well known to those skilled in the art. The device 16 also may have wireless capability to receive and transmit, by telemetry, signals relating to operation of the device. The device 16 may link wirelessly to an external device such as a programmer 24 or to another implanted device such as a sensor 26 of the sensor assembly 10. For sake of clarity, sensor assembly 10 is shown without a fixation member in FIG. 1. See FIGS. 10 and 20. The sensor 26 also may communicate wirelessly with an external receiver 28 to provide in vivo data for selected physiological parameters to an external site to inform clinicians of the patient's status.

FIGS. 2-6 illustrate one embodiment of a sensor assembly 10 adapted for minimally invasive placement in a patient's blood vessel, the assembly being shown in its expanded configuration. The sensor assembly 10 includes a sensor 26 and a fixation member 30 to which the sensor is attached. The fixation member 30 and sensor 26 are arranged to enable the assembly to be collapsed to a low profile to enable it to be carried by a delivery catheter and navigated to a deployment site where it can be released. Upon release, the fixation member expands into engagement with the wall of the blood vessel to secure it in place. The sensor 26 is attached in a manner that when the fixation member 30 is placed the sensor 26, and particularly the sensing element 32 of the sensor 26, are spaced from the wall of the vascular lumen to minimize adverse obstruction to blood flow through the lumen and to position the sensing element 32 of the sensor 26 to be fully exposed to the blood in the vessel, without obstruction from the body of the sensor or the vessel wall.

The sensor 26 includes a housing 34 preferably formed in two sections 36, 38, one of which (36) may contain a battery for powering the electronics and sensor components contained in the other section 38. The housing 34 preferably is of elongate, cylindrical shape with rounded ends and a cylindrical sidewall extending between the ends. This shape is considered to present low resistance to blood flow. Other housing configurations may be employed, however. The sections are formed from a biocompatible material that can be hermetically sealed when the sections 36, 38 are joined. A number of such biocompatible materials may be employed, as will be understood by those familiar with the art, including metals and biocompatible plastics. For example, the sections 36, 38 may be formed from unalloyed titanium with an American Society for Testing and Materials (ASTM) grade 1 to grade 4 or an alloyed titanium (grade 5) that includes aluminum and vanadium. For embodiments in which the sections are metal, the metal should have sufficient malleability to facilitate secure attachment of the housing 34 to the fixation member 30 by crimping, as described in more detail below. The housing as well as some portions of the fixation member may be encapsulated in a biologically inert dielectric barrier material such as a film of silicone or polyp-xylylene) polymer sold under the trademark PARYLENE. Those portions of the housing or fixation member that are intended to serve as poles for intra-body wireless communication (e. g., to transmit or receive RF signals) may remain uncovered.

The fixation member 30 is wire-like and, in this aspect of the invention, is configured to lie substantially in a single plane, indicated generally at 40 in FIG. 3. In the embodiment of sensor 10 illustrated in FIGS. 2 and 3, sensor 26 is mounted to fixation member 30 such that sensor housing 34 and sensing element 32 are intersected by plane 40. In an exemplary embodiment the fixation member 30 may be formed from a highly elastic, biocompatible alloy capable of forming stress induced martensite (SIM). Nitinol (TiNi) is an example of such materials that are also referred to as being "pseudoelastic" or "superelastic." The fixation member 30 shown includes a pair of longitudinally spaced loops 42 connected by an elongate linear attachment strut 44. The loops 42 are spaced apart sufficiently to receive and embrace the sensor 26 with the sensor extending lengthwise along the attachment strut 44. The sensor 26 is attached to the attachment strut 44 to symmetrically lie along the single common plane 40. The fixation member 30, including the attachment strut 44 may be formed from a sheet of material by laser cutting or electro-chemical etching or other fabricating techniques known in the art. The resulting fixation member 30 has a substantially uniform thickness and is formed as a single, integral piece. The wire-like elements that make up the loops 42 and the attachment strut 44 may have a non-circular cross section that may be square or rectangular.

Figure 6:
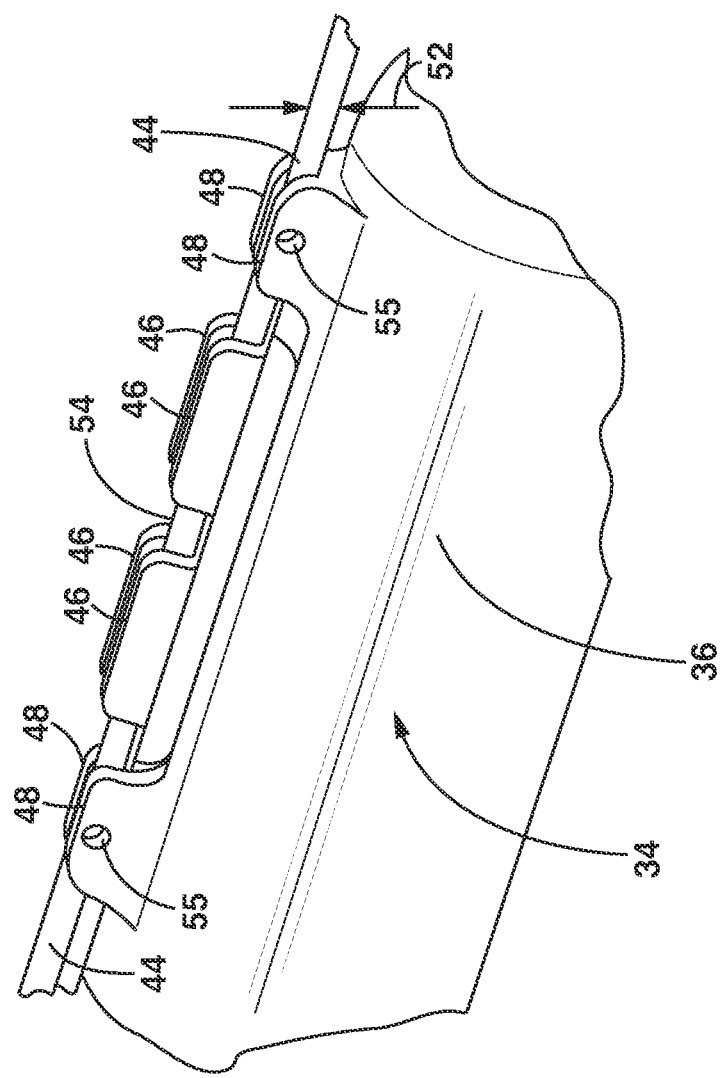
FIG. 6 is an enlarged isometric illustration of the connection between the attachment strut of the fixation member and the sensor housing.
Figure 7:
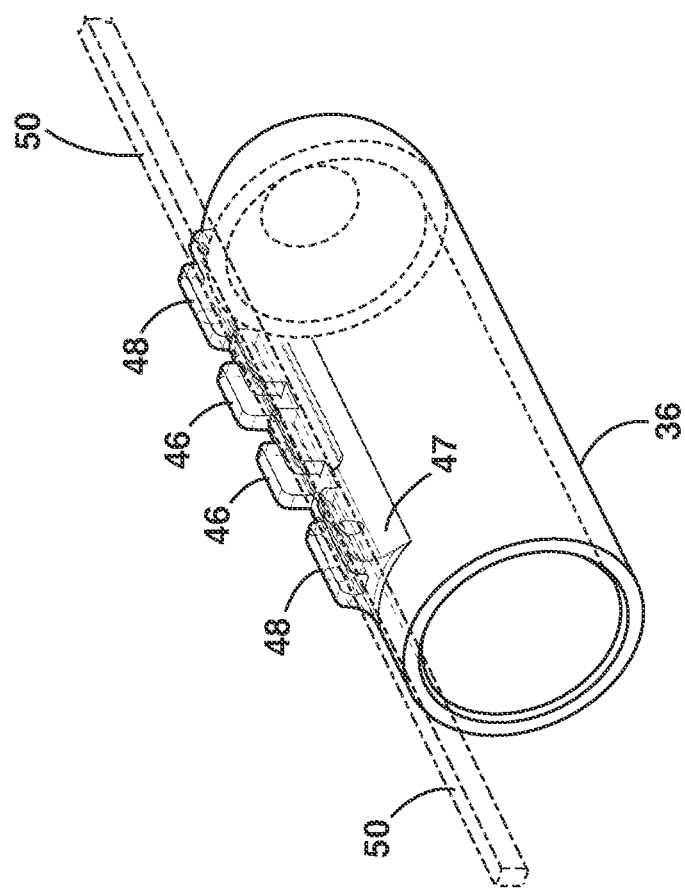
FIG. 7 is an illustration of the battery portion of the housing showing the arrangement of channel-defining tabs.

As illustrated in FIGS. 5-7, the arrangement for attaching the sensor 26 to the strut 44 includes several pairs of tabs 46, 48 formed integrally with the housing 34 preferably on the housing section 36 that contains the battery and at a location that is diametrically opposite the sensing element 32. The pairs of tabs 46, 48 are aligned longitudinally and cooperate to define a longitudinally extending channel 50 that is non-circular in cross-sectional shape (preferably rectangular) and is receptive to attachment strut 44 of the fixation member 30. The width of channel 50 is selected to receive the rectangular cross section of attachment strut 44 in a snug fit to prevent housing 34 from rotating about the axis of attachment strut 44. The tab pairs 46, 48 may be arranged as shown, with two inner pairs 46 disposed between the two endmost pairs 48. The inner tabs 46 extend outwardly from the body of the sensor a distance greater than the outward extension of the endmost tabs 48. The inner tabs 46 will extend beyond the height 52 of the attachment strut 44 so that when strut 44 is seated in channel 50 the ends of the inner tabs 46 may be crimped over strut 44 as shown in FIG. 5. The endmost tab pairs 48 may extend less than the crimping tabs 46 and serve only to define the channel 50 and guide attachment strut 44 into the channel 50. As shown in FIG. 6, endmost tab pairs 48 need not extend beyond the exposed surface 54 of strut 44. The tabs may be provided with detent elements 55 (FIG. 6) to facilitate alignment with the tabs of a crimping tool having complementary elements (not shown).

By way of dimensional example the thickness of fixation member 30 may be of the order of about 0.012 inch, including attachment strut 44. The width of channel 50 may be of the order of about 0.0125 inch. The height of strut 44 may be of the order of about 0.015 inch. The crimp tabs 46 may be slightly higher than the height of the attachment strut by an amount to enable their ends to be crimped over the attachment strut. The tabs may be about 0.008 inch thick and 0.040 inch long. The guide tabs 48 may be somewhat longer than the crimp tabs 46, for example, about 0.055 inch, and their height may be about the same as that of the strut 44. As illustrated in FIG. 7, the battery segment 36 of the housing, on which the tabs are mounted, may include a slightly raised pad 47 that defines the bottom of channel 50 and from which the tabs extend. Sensor housing 34 may be spaced from strut 44 by the thickness of raised pad 47. It should be understood that the arrangement of tabs, including their number and dimensions may be varied as desired to provide an arrangement by which a linear attachment strut, non-circular in cross section, may be inserted transversely into the channel 50 and crimped in place by tabs. It should be understood, however, that although the foregoing embodiment is presently preferred, other connector arrangements might be employed while still retaining other aspects of the invention described herein. For example, such connector arrangements may include tubular connectors as described in provisional application Ser. No. 61/408,073, filed Oct. 29, 2010 and entitled Medical Device Fixation Attachment Mechanism, the disclosure of which is incorporated herein by reference.

Figure 2:
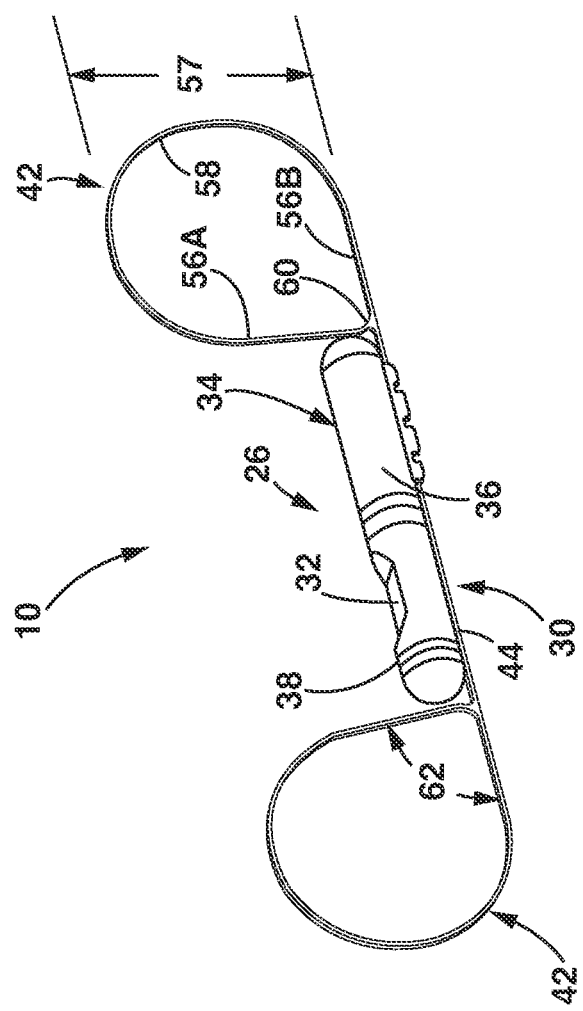
FIG. 2 is an isometric illustration of one embodiment of a sensor assembly embodying the invention in an expanded configuration.
Figure 8:
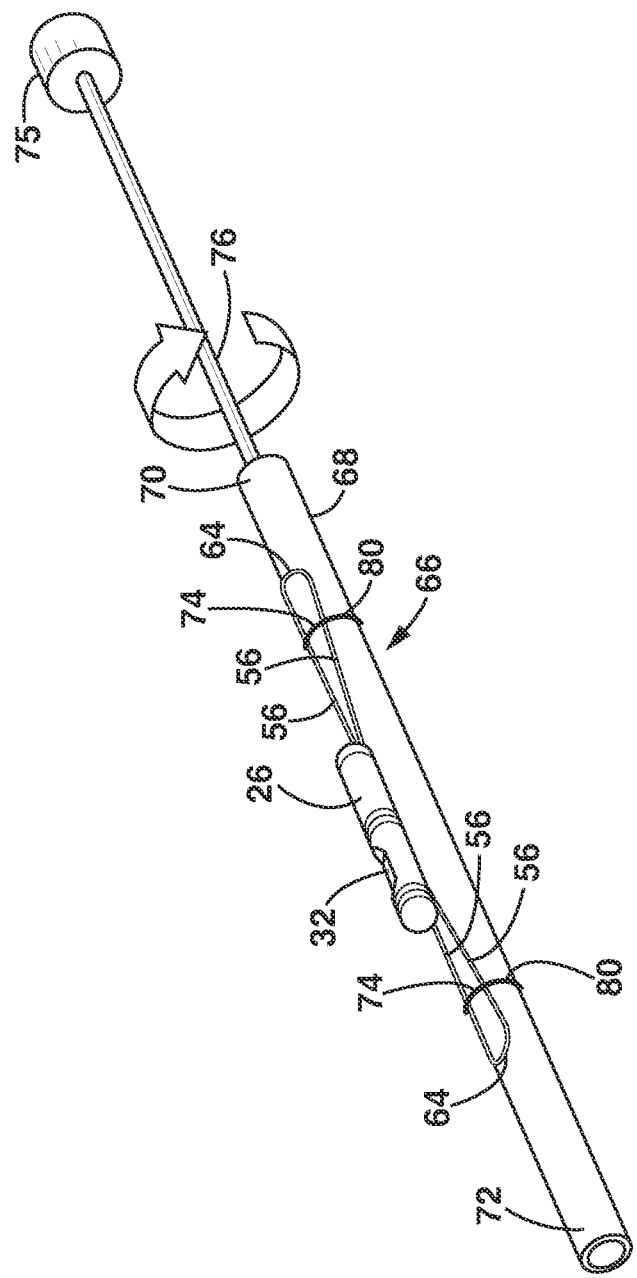
FIG. 8 is a diagrammatic illustration of one embodiment of a delivery device that may be used to deliver and deploy a sensor assembly having a single plane fixation member.
Figure 10:
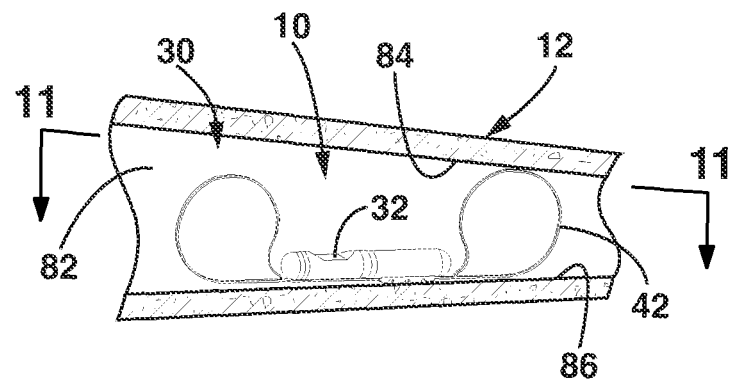
FIG. 10 is a diagrammatic side elevation of the sensor assembly of FIG. 2 deployed in a pulmonary artery of a patient.

FIG. 8 illustrates the low profile configuration of the sensor assembly in which fixation member 30 with sensor 26 attached is compressed to a narrower shape having a smaller effective cross section in which it may be mounted to and delivered by a delivery device 66 to an intended deployment site such as the pulmonary artery. In this configuration each of the loops 42 is compressed from its relaxed, expanded shape to a more elongated shape defined by loop segments 56 that are drawn more closely parallel to each other. Although fixation member 30 is formed from a superelastic material such as superelastic nitinol having the ability to undergo extreme strain without permanent deformation, it is desirable to shape the loops 42 to reduce the risk of plastic deformation when compressing the loops to the low profile delivery configuration. To that end we have found that forming the loops 42 in a teardrop shape results in a reduced strain in the region of the juncture of the loop 42 with the attachment strut 44. Thus, as shown in FIG. 2 each loop 42 may be considered as having loop segments 56A and 56B connected to each other by a bight segment 58 that circumscribes an arc of approximately 180 degrees. Loop segment 56B may be considered as a linear extension of attachment strut 44. Loop segment 56A is generally linear and is attached to the inner region of the loop segment 56BA at a junction 60. The angle 62 made by the loop segments 56A and 56B at the junction 60 is substantially smaller than the angle subtended by the arc of the bight 58 resulting in teardrop shaped loop 42. In the embodiment illustrated in FIG. 2, junction angle 62 may be of the order of about 90 degrees, less than the arc of about 180 degrees defined by the bight. Alternatively, in the embodiment illustrated in FIG. 10, loop segment 56A may include a portion having a curve that is reversed from that of bight 58 such that junction angle 62 may be of the order of about 45 degrees. In the embodiment of FIG. 10, bight segment 58 may circumscribe an arc greater than 180 degrees and loop segment 56A may have no straight portion. When fixation member 30 is compressed to bring the loop segments 56A, 56B into a more parallel low profile configuration the loop segment 56A will be bent through a relatively smaller arc of about 90 degrees or less although at a relatively small radius. By limiting the arc through which the loop segment 56A must bend the risk of plastic deformation in the region of the junction is reduced. While the extremity 64 of the bight segment 58 of the loop 42 will bend through a greater arc, the radius of the compressed bend at the extremity 64 is greater than that at the junction 60 as shown in FIG. 8.

Figure 9A:
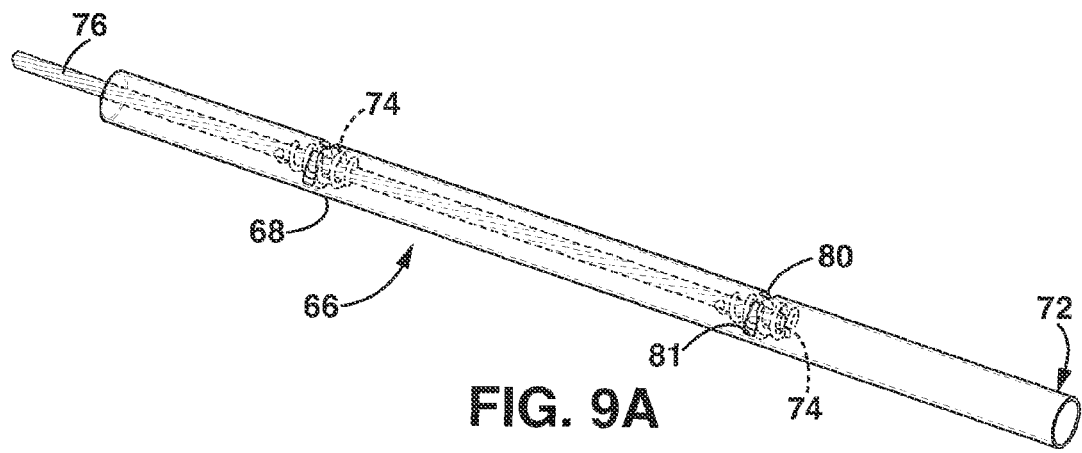
FIG. 9A is an illustration of a portion of the delivery catheter of FIG. 8, partly broken away and with the sensor assembly removed for clarity.
Figure 9B:
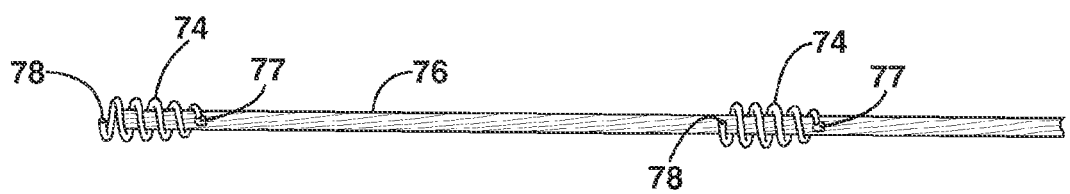
FIG. 9B is a diagrammatic illustration of the rotatable shaft of the delivery device by which the sensor assembly is retained and released.
Figure 9E:
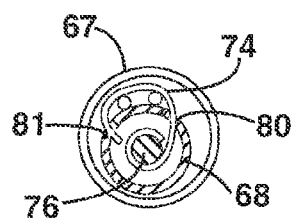
FIG. 9E is a sectional illustration as seen along the line 9E-9E of FIG. 9D.
Figure 9F:
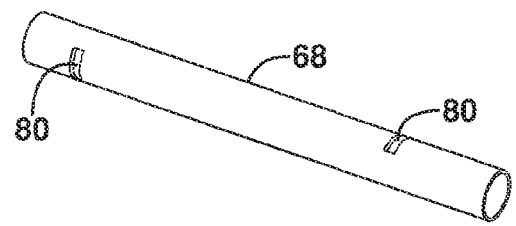
FIG. 9F is an illustration of a portion of the delivery device modified to have circumferentially displaced apertures to enable the proximal and distal portions of the fixation members to be released in sequence.
Figure 9D:
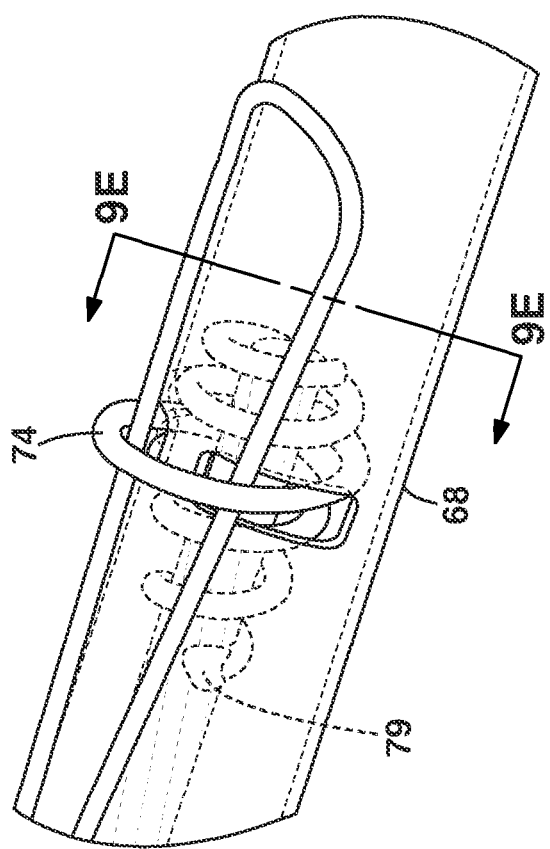
FIG. 9D is an illustration similar to FIG. 9C showing the delivery device with the shaft having been rotated to cause the helical coil to securely engage the fixation member of the sensor assembly to the delivery shaft.
Figure 9C:
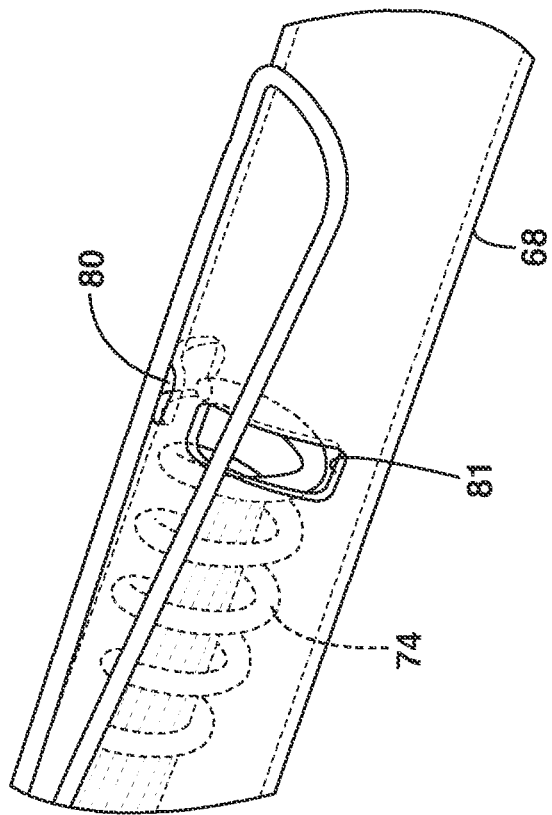
FIG. 9C is an enlarged isometric illustration of a portion A of the delivery device of FIG. 9A, partly in section, showing a loop of the fixation member of the sensor assembly in its low profile configuration in readiness to be attached to the delivery device.

FIGS. 9A-9E depict, diagrammatically and in fragmented illustration, an example of a delivery device shown as in FIG. 8 that may be used to deliver and deploy the sensor assembly 10 in a selected vessel. Delivery device 66 may also be used to deliver sensor assembly 87, described further below. The delivery device 66 is in the form of an elongate outer tubular catheter shaft 68 having proximal and distal ends 70, 72 with the sensor assembly 10 mounted on the outer surface of the distal region of the catheter 68 in its compressed, low profile configuration (FIG. 8). The shaft 68 should be formed from a material and dimensioned to have sufficient flexibility to be navigated through the patient's vasculature to the intended deployment site. The device may be guided through a guide catheter or in association with a guide wire, as is well known to those skilled in the art. The sensor assembly may be releasably retained on the catheter shaft by an arrangement of rotatable helical retention elements 74 attached to a rotatable inner shaft 76 (FIGS. 9A-9F) housed within the catheter 68. Each of the helical retention elements is disposed about the shaft 76 and has one end 77 secured to the shaft 76, as by adhesive 79 or other suitable means, and another, free end 78. The catheter shaft 66 has at least one exit aperture 80 and preferably two apertures 80, also a reentry aperture 81 through which the free end 78 of each retention element 74 can pass. As shown in FIGS. 9C and 9D the shaft 76 can be rotated to enable a retainer portion, including the free end 78 of the retention coil 74 to protrude out of the exit aperture 80 and pass over a compressed loop 42 of the fixation member to retain the loop on the catheter until deployment. The helical coil is sufficiently flexible and resilient so that the turn that passes over the fixation member can resiliently increase in diameter to accommodate the fixation member. Providing the second aperture 81 through which the free end 78 of the retention member may reenter the catheter shaft may add to the security by which the sensor assembly is retained on the catheter shaft. A helical retention element 74 is provided for each of the proximal and distal loops 42.

The delivery device may be advanced through a guide catheter or sheath 67 (FIG. 9E) that may be retracted to expose the sensor assembly. When the delivery catheter has been positioned as desired and the sensor assembly is to be deployed, the shaft 76 is rotated, as by a control knob 75 attached to the proximal end of the rotatable shaft (FIG. 8), to rotate the helical retention elements 74 and retract the retainer portions and free ends 78 into the catheter shaft, thus releasing the sensor assembly. As the sensor assembly is released it self-expands to its expanded configuration within the vessel. The retention elements 74 may be arranged to release both the proximal and distal loops simultaneously or may be arranged to release one before the other, for example, to release the distal loop 42 first, to observe its position and confirm it is in the intended location in the vessel. That may allow for repositioning the distal loop 42, after which the proximal loop 42 may be deployed. Repositioning may be accomplished by advancing the guide catheter or sheath distally to recapture the distal loop 42 while the unreleased retention member retains the position of the sensor assembly. The recaptured sensor assembly then may be repositioned and redeployed. It may be noted that although the loop segments 56A and 56B are approximately parallel when in their low profile configuration they do diverge slightly towards their respective bights 91. The divergence may cause a wedging effect to secure the proximal retention member and the proximal loop as the guide catheter or sheath is advanced distally to recapture the sensor assembly.

The sequence of release of the loops 42 may be determined by the relative circumferential location of the retention elements 74 and their spiral ends 78 and the location of the openings 80, 81 or by arranging the helical retention coils 74 on shaft 76. Alternately the release sequence can be varied by providing one of coils with more turns between its free end and the turn that engages its associated fixation member loop than the other of the coils. The retention member with the fewer number of free turns will be first to release its associate loop. For example, by arranging the distal coil to have fewer free turns than the proximal coil, the distal loop 42 will be released first enabling the clinician to determine if the sensor is properly positioned.

The delivery device may be advanced to the intended deployment site by advancing it through a guide catheter or may be guided over a guide wire in an over-the-wire system, both of which are familiar to those skilled in the art. It should be understood that delivery device 66 is only one example of a delivery system for sensor assembly 10. Other types of delivery systems can be utilized, such as an outer sheath (not shown) slidably disposed around the sensor assembly to constrain the sensor assembly in its low profile configuration until a pusher mechanism ejects the sensor assembly from the distal end of the sheath. It should be noted that the superelastic construction of the fixation member enables it to be elastically distorted from its planar expanded shape to a shape adapted to fit onto or within a delivery catheter.

Figure 11:
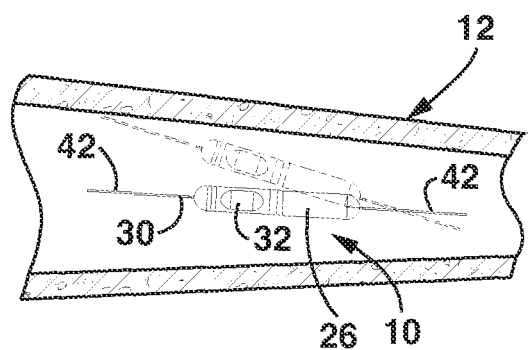
FIG. 11 is a diagrammatic illustration, in plan, of the deployed sensor as seen along the line 11-11 of FIG. 10.
Figure 12:
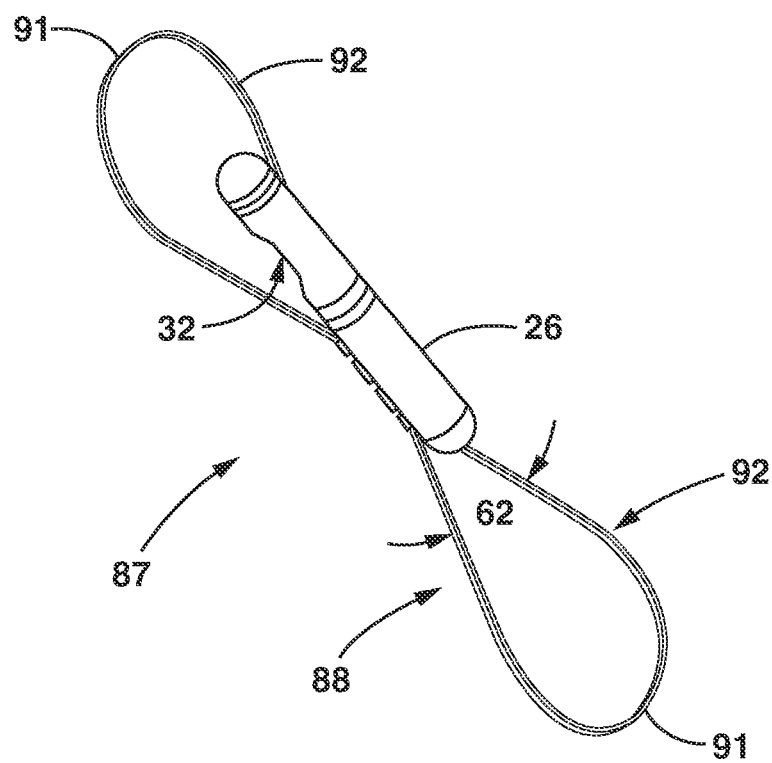
FIG. 12 is an isometric illustration of another embodiment of a sensor assembly having a modified fixation member.
Figure 13:
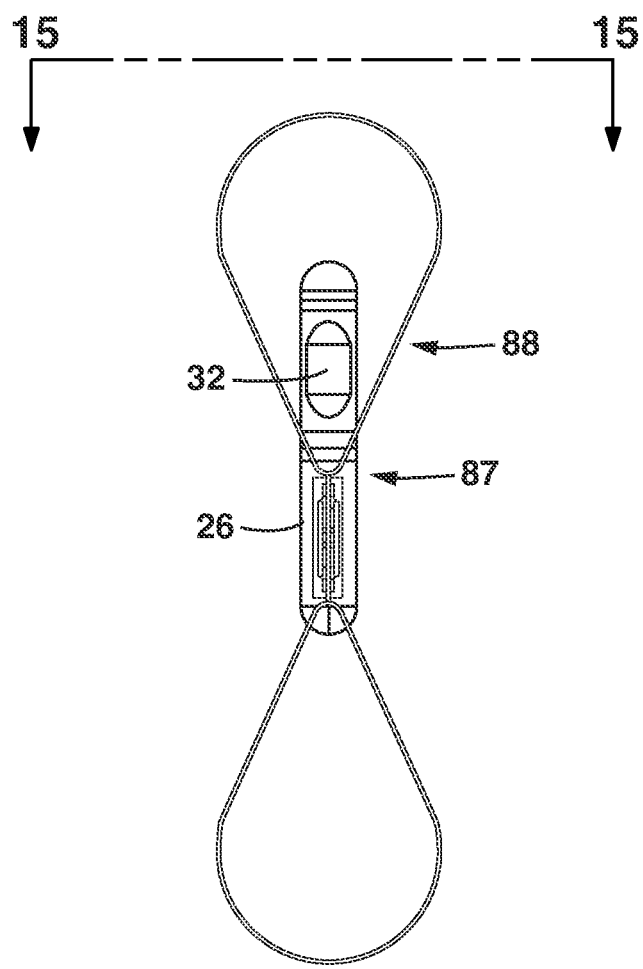
FIG. 13 is a diagrammatic plan view of the embodiment of the sensor assembly of FIG. 12 as viewed from its underside, showing the connection between the fixation member and sensor housing.
Figure 14:
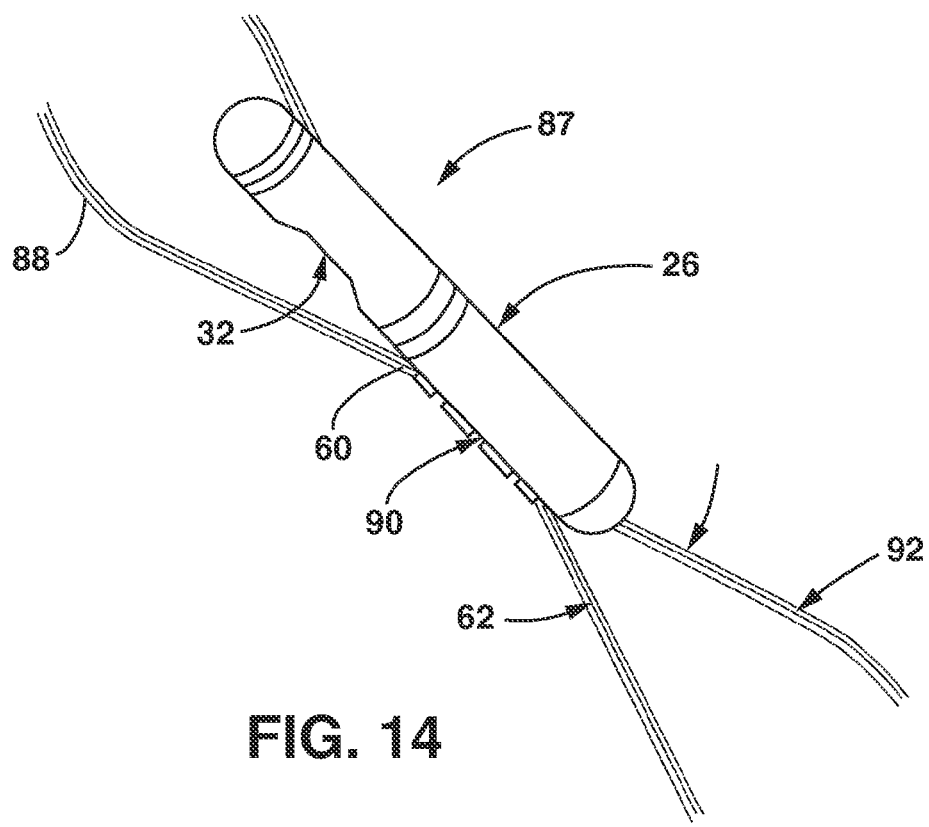
FIG. 14 is a an enlarged illustration of the underside of the sensor assembly of FIG. 13 viewed from a different angle.

FIGS. 10 and 11 illustrate, diagrammatically, the positioning of the sensor assembly 10 in a pulmonary artery 12. The human main pulmonary artery 12 is relatively short and often has a lumen 82 that tapers in the direction of blood flow. The degree of taper may vary from patient to patient, with patients suffering from chronic heart failure tending to have more severe taper with higher pulmonary blood pressures. The main pulmonary artery branches into left and right pulmonary arteries and whether the clinician will elect to place a device in the main artery or one of the branches of the pulmonary artery tree will depend on the anatomy and condition of the particular patient among other factors. When deploying the sensor assembly 10 the delivery catheter is positioned so that the more distal of the loops 42 will be located in the selected portion of the selected artery in which the distal loop 42 will expand to engage the luminal surface 84, 86 of the vessel wall with only sufficient force to hold the sensor assembly in place. Loop 42 is expected to apply little more than the force that is appropriate to hold the device in place without applying excessive force to that surface. The fixation member 30 should be constructed to apply light but sufficient force to the vessel. The forces to be applied are substantially less than those associated with the placement of vascular stents in which the objective is to press against the vascular wall with sufficient force to provide scaffolding support for the vessel wall. By contrast, the present invention is intended merely to maintain the sensor assembly 10 in the vessel without migrating upstream or downstream while supporting the sensor 26 in its intended position and orientation. When the sensor assembly 10 is deployed the fixation member 30 expands to its single plane with the most distal loop expanding to a dimension to engage the luminal wall of the vessel. Regardless of the orientation of the assembly during deployment the loop 42 will seat itself to engage substantially diametrically opposite surfaces 84, 86 of the vessel wall with the attachment strut 44 extending along one of those surfaces. In that deployed position, the sensing element 32 of the sensor 26 will be oriented to face the center of the lumen to be exposed fully and without obstruction to blood flow in the lumen. It may be noted that in tapered vessels such as in a sharply tapered pulmonary artery the proximal of the loops 42 may not engage diametrically opposite surfaces of the vessel wall. In such circumstances the blood flow in the artery may cause the sensor assembly to pivot about its points of contact of the distal loop 42 with the vessel wall as suggested in phantom in FIG. 11. While that may cause the proximal loop 42 to swing sideways the proximal loop 42 will engage the vessel wall to maintain the sensor 26 spaced from the wall.

The sensor assembly is placed by advancing the delivery catheter to a selected location within the vessel and deploying the sensor assembly so that it remains secure in the vessel at that location. To that end, the expanded dimensions of the fixation member are selected to be slightly greater than a predetermined transverse dimension ("effective diameter") of the vessel into which it is to be placed. By way of example, for a device formed from a superelastic material intended for placement in a pulmonary artery, the fixation member preferably may have an expanded dimension about twenty percent greater than the effective diameter at the selected location of the artery. Where the device is to be placed. While the dimensions and anatomies of the pulmonary arterial tree necessarily vary among patients, particularly heart failure patients, we consider that many, perhaps most candidates for such devices are likely to have a region of the arterial tree with an effective diameter of about ten millimeters. Therefore, and by way of example, the fixation member preferably has a distal loop with a relaxed height 57 (FIG. 2) of about twelve millimeters. When placing the device, the clinician determines and selects a suitable location in the patient's arterial tree with an effective diameter of about ten millimeters, navigates the delivery catheter to locate the sensor assembly at that location and then releases the assembly so that it expands into sufficient engagement with the vessel to prevent migration. The characteristics of the superelastic material and dimensions of the fixation member should be selected so that the force applied by the deployed fixation member to the artery wall causes no adverse trauma while fixing the device in place.

Figure 15:
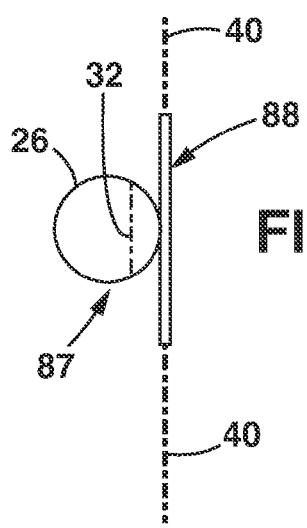
FIG. 15 is a diagrammatic end view of the sensor assembly of FIG. 12 as seen along the line 15-15 of FIG. 13.
Figure 16:
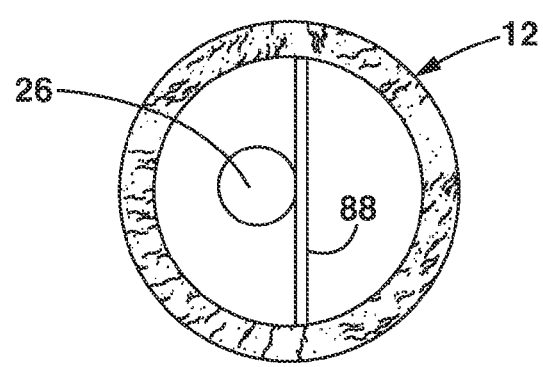
FIG. 16 is a diagrammatic end view of the device of FIG. 12 illustrating the position of the device when deployed in a vessel.
Figure 17:
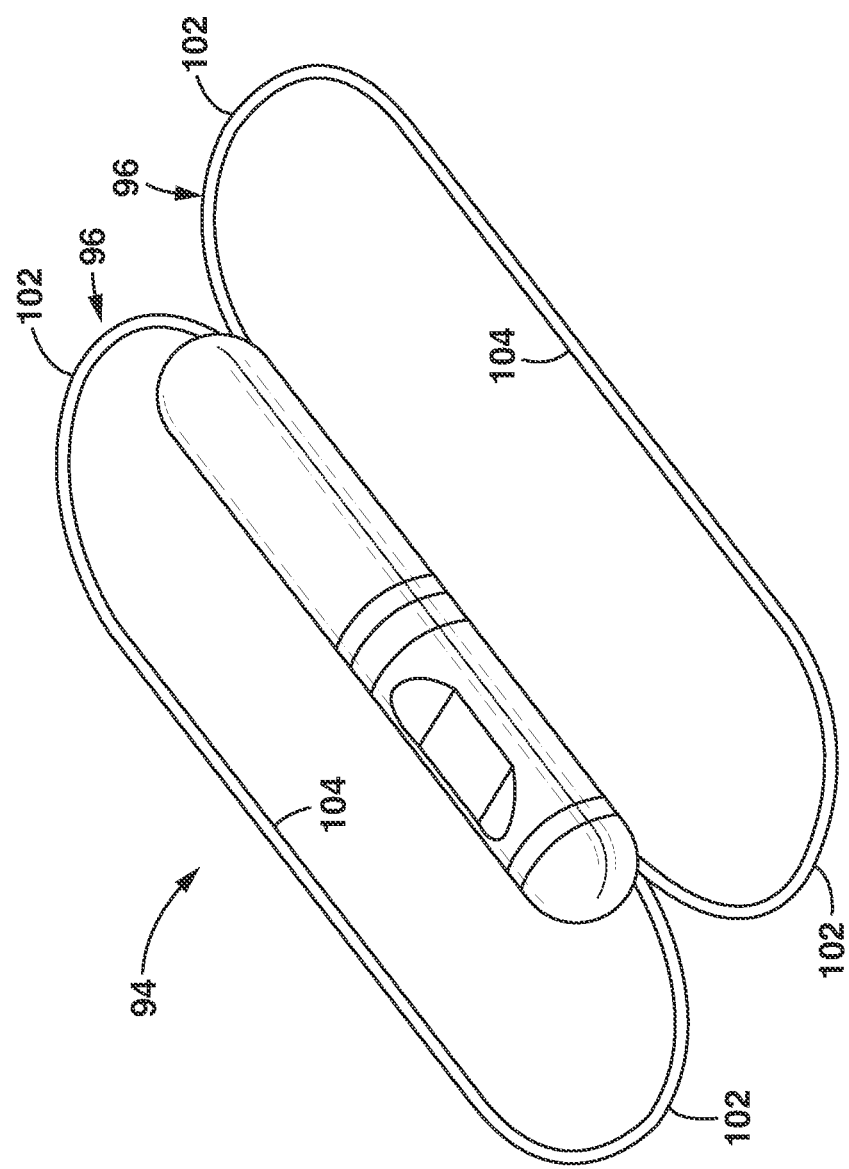
FIG. 17 is an isometric illustration of another embodiment incorporating aspects of the invention.
Figure 18:
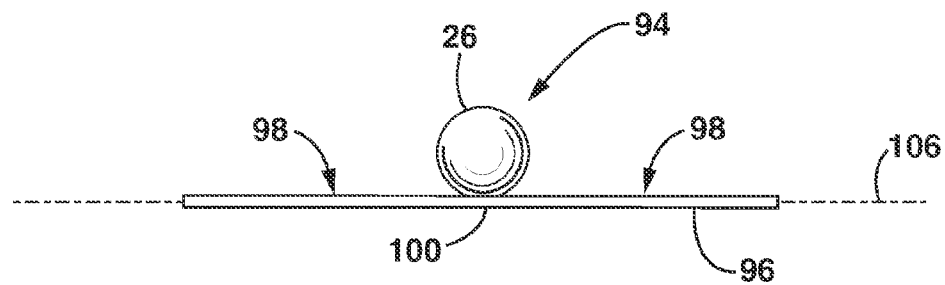
FIG. 18 is an end view of the embodiment of FIG. 17.
Figure 19:
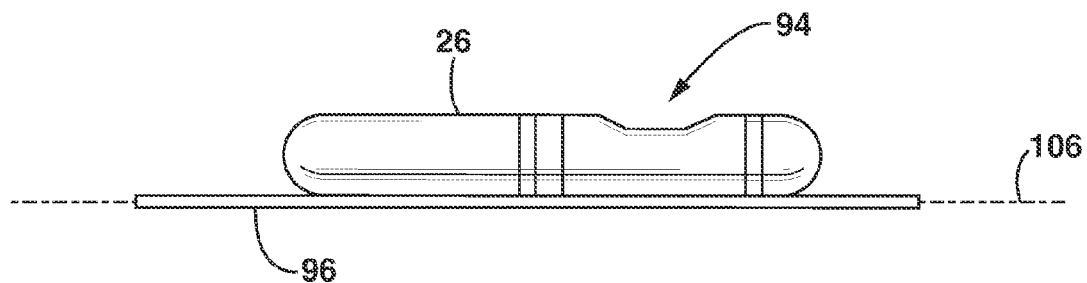
FIG. 19 is a side view of the embodiment of FIG. 17

FIGS. 12-16 illustrate another example of a sensor assembly 87 embodying the invention in which the fixation element 88 and sensor 26 are arranged to support the sensor more centrally in the vascular lumen. In this embodiment the attachment strut 90 (FIG. 14) may be shorter than that of the embodiment of FIG. 2 and the sensor 26 is supported to one side of the plane 40 (FIG. 15). Additionally, the teardrop-shaped loops 92 may be configured to have a smaller junction angle 62 because the junctions 60 of the loops 92 can be located closer to each other. As described above, the reduced junction angle 62 reduces the amount of strain on the junction 60 when compressing the fixation member to a low profile configuration. FIG. 16 illustrates, diagrammatically, the manner in which the fixation member 88 supports sensor 26 when deployed in a vessel, for example, a pulmonary artery 12. As with the example of FIG. 2, upon release in the artery, fixation member 88 expands to engage the vessel wall at approximately diametrically opposed locations. In this embodiment sensor 26 is oriented to the side of the single common plane 40 of the fixation member 88 (FIG. 15) and will be supported to extend longitudinally of the vessel and approximately in the middle of the vessel lumen. The outermost extremities 91 of the loops 92 preferably extend sufficiently beyond the ends of sensor 26 so that even if the proximal end of the assembly shifts laterally toward the wall of the vessel, the proximal one of the loops 92 will contact the wall before the sensor to maintain the sensor spaced apart from the wall. The manner of attachment of sensor 26 to fixation member 88 may be substantially the same as described above. Attachment strut 90 in this embodiment need only be long enough to be received in channel 50 of the sensor. The sensor assembly may be mounted to a delivery device as described above.

Figure 20:
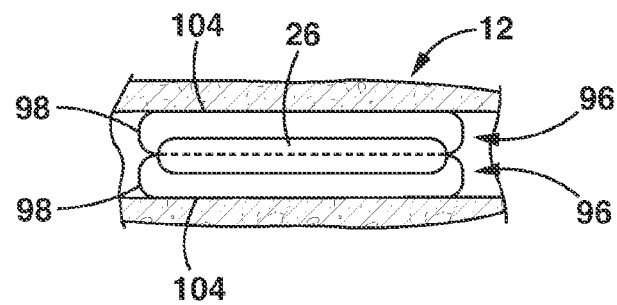
FIG. 20 is a diagrammatic illustration of the embodiment of FIG. 17 deployed in a blood vessel.
Figure 21:
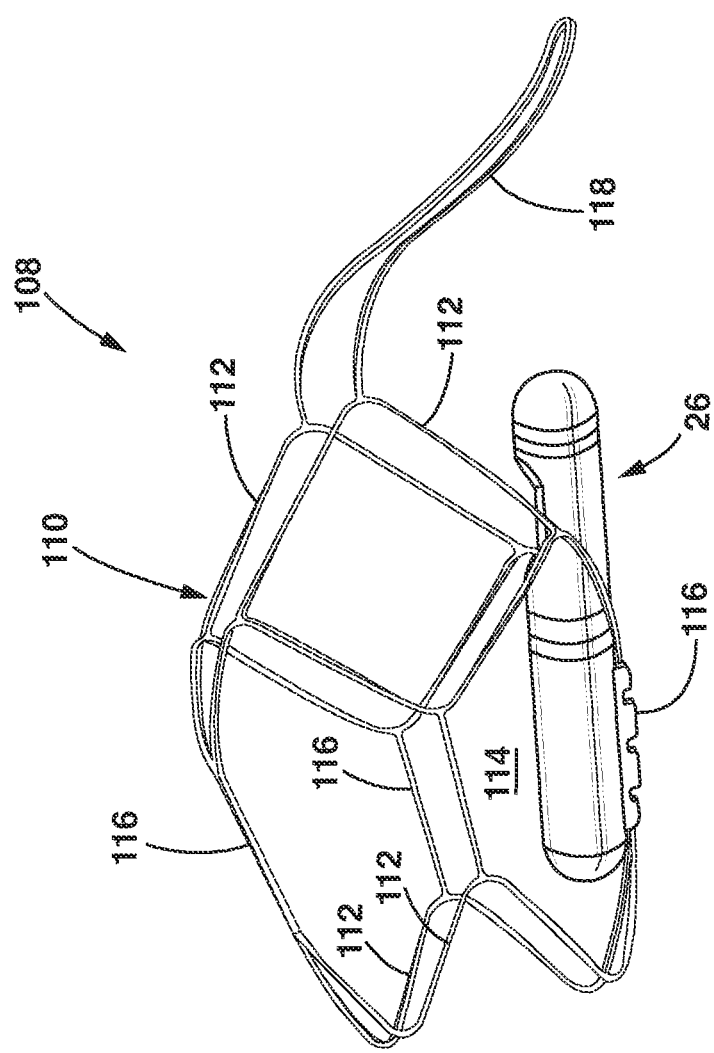
FIG. 21 is an illustration of a sensor assembly having a tubular fixation member with the sensor housing attached in accordance with one aspect of the invention.
Figure 22:
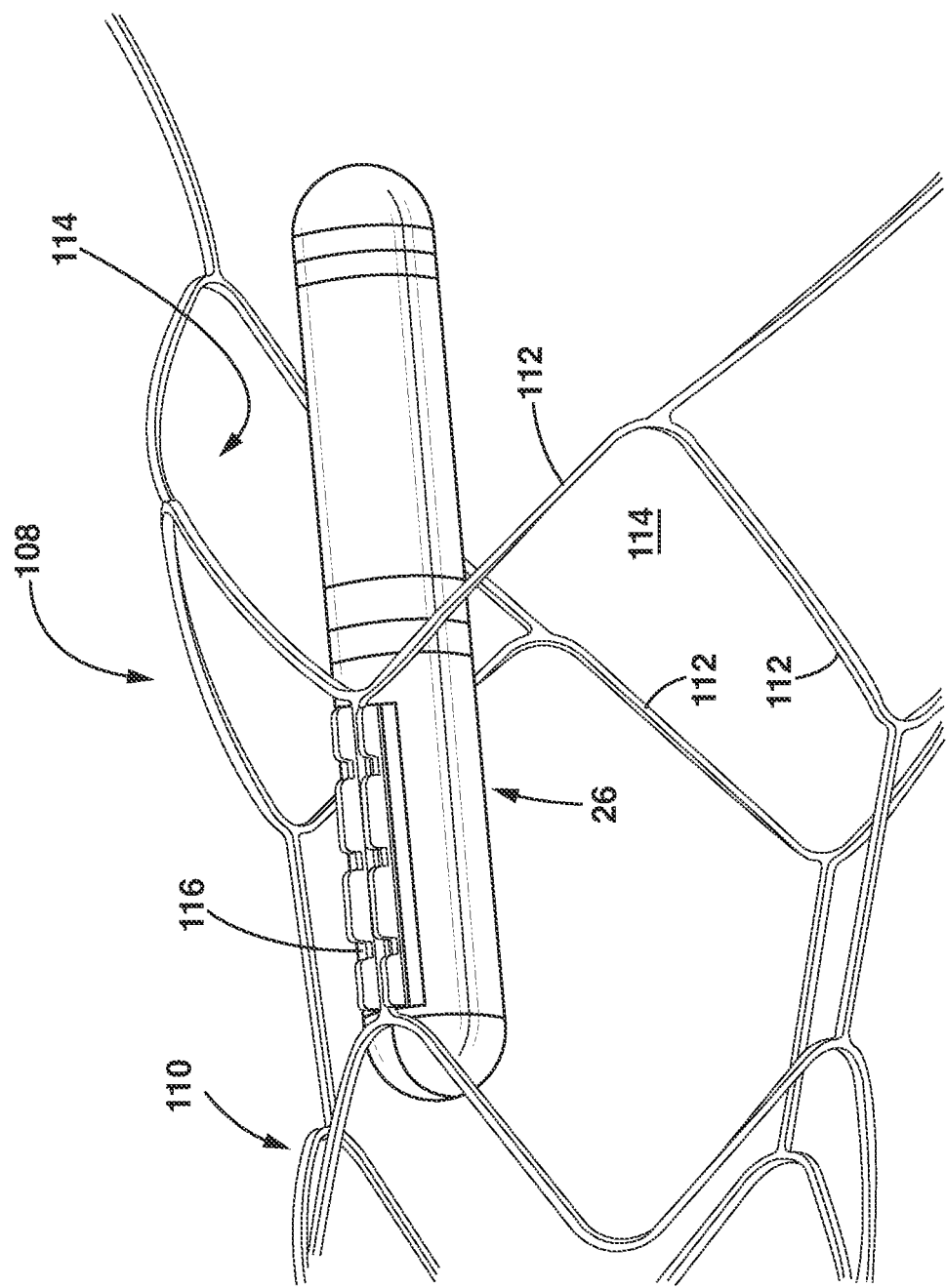
FIG. 22 is an enlarged illustration of a portion of the sensor assembly of FIG. 21 showing the connection between the sensor housing and the fixation member.

FIGS. 17-20 illustrate a further example of a sensor assembly 94 embodying principles of the invention. In this example the fixation member 96 includes a pair of oval loops 98 disposed in side-by-side relation joined by a common attachment strut 100. Each loop 96 includes an arcuate bight 102 at each of its ends and a longitudinally extending side strut 104. In their expanded configuration the loops 96 lie substantially in a single plane 106. When deployed in a vessel, as suggested diagrammatically in FIG. 20 the side struts 104 of the oval loops 98 may engage diametrically opposed portions of the vessel wall and support the sensor capsule 26 substantially centrally in the lumen of the vessel. In this embodiment sensor 26 is oriented to the side of the single common plane 106 of the fixation member 88 (FIG. 18) and will be supported to extend longitudinally of the vessel and approximately in the middle of the vessel lumen. A diagrammatic end view of the device of FIG. 20 illustrating the position of the device when deployed in the vessel would appear similar to the illustration shown in FIG. 16. Because struts 104 of fixation member 96 engage opposed elongate, longitudinally extending portions of the luminal surface of the vessel wall, the position and orientation of the fixation member 96 and sensor housing 26 provide additional resistance to reorientation of sensor assembly 94 to a canted position. Thus, the length of fixation member 96 may be reduced in this example to be only slightly longer than the sensor capsule 26 FIG. 19. Here, too, the sensor assembly may be mounted to a delivery device configured to accommodate the fixation member 96 of the sensor assembly Certain aspects of the invention also may be incorporated into other sensor assemblies in which the fixation member may take forms other than the single plane examples described above. For example, FIGS. 21 and 22 illustrate a sensor assembly 108 with a fixation member 110 having a generally tubular expanded shape that is compressible to a low profile tubular shape to facilitate catheter delivery. The fixation member is defined by a plurality of links 112 arranged to define expandable cells 114. Such tubular fixation elements may be fabricated using any of a variety of well known techniques commonly employed for fabricating tubular stents, for example, by laser cutting the pattern of the fixation member from a tube of the selected material. In accordance with one aspect of the present invention such tubular fixation members 110 may incorporate at least one longitudinally extending, linear strut 116 having a non-circular cross section and integrally joined at its ends to other elements of the fixation member 110 so that it may serve as an attachment strut to which a sensor capsule 26 may be secured. As shown in the drawings the sensor capsule 26 may be the same as that described above in connection with the example of FIG. 2 with tabs arranged to define a channel 50 receptive to the linear attachment strut 116. Assembly of the fixation member 110 and sensor capsule 26 is the same, namely, inserting the strut 116 transversely into the channel 50 and crimping the crimp tabs to secure the parts together. The tubular fixation member may be delivered to the deployment site by a catheter having a tubular chamber at its distal end adapted to receive the sensor assembly in a collapsed, low profile configuration similar to such delivery systems used with vascular stents. The fixation member 108 may include a tether 118 by which the device may be drawn into an opening at the distal end of the delivery catheter while progressively collapsing the fixation member to a low profile delivery configuration.

It should be understood that the foregoing examples of embodiments of the invention are illustrative only and that other embodiments, modifications and equivalents may be apparent to those skilled in the art that nevertheless are within and embody the principles of the invention.

We claim:

1. An implantable sensor assembly adapted for placement in a selected region of a human pulmonary artery tree, the assembly comprising:
    a wire-like fixation member self-expandable from a low profile configuration to an expanded configuration and formed to lie in a single plane when expanded, the wire-like fixation member further adapted to engage the wall of a patient's blood vessel to thereby maintain a position of the sensor assembly in the vessel, the fixation member having proximal and distal ends, at least the distal end comprising a distal loop having a relaxed height approximately twenty percent greater than a predetermined effective diameter at the selected region, and an elongate, linear attachment strut extending proximally from the distal loop such that the distal loop and strut lie substantially in the single plane; and
    a sensor housing containing sensing elements adapted to sense a physiological parameter within the patient's vessel, the housing having proximal and distal ends and a longitudinal sidewall extending between the ends;
    wherein the sensor housing includes a connector extending along the longitudinal sidewall, the connector being attached securely and directly to the attachment strut.

2. The implantable sensor assembly as defined in claim 1 further comprising a proximal loop formed at the proximal end of the fixation member, the proximal loop being connected to the proximal end of the attachment strut and lying substantially in the single plane.

3. The implantable sensor assembly as defined in claim 2 wherein the attachment strut is sufficiently long to enable the sensor housing to be disposed between and embraced by the proximal and distal loops.

4. The implantable sensor assembly as defined in claim 1 wherein the sensor housing is attached to the attachment strut to intersect the single plane.

5. The implantable sensor assembly as defined in claim 1 wherein the connector and attachment strut are configured to prevent relative rotation of the housing about the strut.

6. The implantable sensor assembly as defined in claim 3 wherein the sensor housing has an externally exposed sensing element, the sensing element being intersected by the single plane.

7. The implantable sensor assembly as defined in claim 2 wherein each of the distal and proximal loops has a teardrop shape when the fixation member is in the expanded configuration, the teardrop shape having a narrow end disposed at a junction of the loop and the attachment strut.

8. The implantable sensor assembly as defined in claim 7 wherein the teardrop shape is defined by a pair of loop segments connected by a bight segment, the inner ends of the loop segments meeting at the junction in an angle that is no greater than about 90 degrees.

9. The implantable sensor assembly as defined in claim 1 wherein the fixation member has superelastic properties.

10. The implantable sensor assembly as defined in claim 9 wherein the fixation member comprises a nitinol alloy.

11. The implantable sensor assembly as defined in claim 1 wherein the predetermined effective diameter is about ten millimeters and the height of the distal loop is about twelve millimeters.

12. The implantable sensor assembly as defined in claim 1 wherein the connector is formed integrally with the housing.

13. The implantable sensor assembly as defined in claim 1 wherein the distal loop is continuous.

\* \* \* \* \*